United States Patent
Kim et al.

(10) Patent No.: US 7,531,138 B2
(45) Date of Patent: May 12, 2009

(54) DEVICE AND METHOD FOR RAPIDLY LYSING CELLS OR VIRUSES

(75) Inventors: Su-hyeon Kim, Seoul (KR); Jeong-gun Lee, Seoul (KR)

(73) Assignee: Samsung Electronics Co., Ltd. (KR)

( * ) Notice: Subject to any disclaimer, the term of this patent is extended or adjusted under 35 U.S.C. 154(b) by 60 days.

(21) Appl. No.: 11/560,890

(22) Filed: Nov. 17, 2006

(65) Prior Publication Data

US 2008/0014122 A1    Jan. 17, 2008

(30) Foreign Application Priority Data

Nov. 24, 2005   (KR) ................. 10-2005-0112967

(51) Int. Cl.
 *B01L 3/00* (2006.01)
 *G01N 1/00* (2006.01)
 *C12M 1/00* (2006.01)
(52) U.S. Cl. .............. 422/99; 436/174; 435/293.1; 422/112; 137/87.01
(58) Field of Classification Search ............ 422/99, 422/112; 435/293.1; 436/174; 137/87.01
See application file for complete search history.

(56) References Cited

U.S. PATENT DOCUMENTS

| | | | | |
|---|---|---|---|---|
| 4,266,559 | A | * | 5/1981 | Akhavi ............ 600/579 |
| 4,882,284 | A | * | 11/1989 | Kirchanski et al. ........ 436/63 |
| 5,234,809 | A | | 8/1993 | Boom et al. |
| 5,403,710 | A | | 4/1995 | Weisburg et al. |
| 5,705,628 | A | | 1/1998 | Hawkins |
| 5,897,842 | A | * | 4/1999 | Dunn et al. ............ 422/131 |
| 6,156,576 | A | | 12/2000 | Allbritton et al. |
| 6,251,660 | B1 | * | 6/2001 | Muir et al. ............ 435/287.2 |
| 6,335,201 | B1 | | 1/2002 | Allbritton et al. |
| 6,450,203 | B1 | * | 9/2002 | Backhouse et al. ......... 137/807 |
| 6,685,730 | B2 | | 2/2004 | West et al. |
| 6,748,332 | B2 | * | 6/2004 | Chen ............ 702/19 |
| 7,192,560 | B2 | | 3/2007 | Parthasarathy et al. |
| 2002/0028471 | A1 | * | 3/2002 | Oberhardt ............ 435/7.21 |

(Continued)

OTHER PUBLICATIONS

Deggerdal et al.; "Rapid Isolation fo PCR-Ready DNA from Blood, Bone Marrow and Cultured Cells, Based on Parmagnetic Beads" Biotechniques; vol. 22; pp. 554-557; Mar. 1997.

(Continued)

*Primary Examiner*—Walter D Griffin
*Assistant Examiner*—Natasha Young
(74) *Attorney, Agent, or Firm*—Cantor Colburn LLP

(57) ABSTRACT

A cell lysis device for lysing cells or viruses, comprising a cell lysis tube having a sample inlet; a pump connected to the cell lysis tube for transferring a sample into the tube; a sealing unit for reversibly sealing a specific region of the tube; and a laser source for generating a laser is provided. Further, a method of lysing cells or viruses using the cell lysis device is provided. The method comprises introducing a sample containing cells or viruses and optionally magnetic beads to the cell lysis tube through the sample inlet; transferring the sample to a specific region in the cell lysis tube by means of the pump; temporarily sealing the region of the cell lysis tube where the sample is placed with the sealing unit; irradiating the sample with the laser; removing the sealing unit from the cell lysis tube; and discharging the sample from the cell lysis tube by means of the pump.

21 Claims, 3 Drawing Sheets

U.S. PATENT DOCUMENTS

| | | | |
|---|---|---|---|
| 2003/0095897 A1 | 5/2003 | Grate et al. | |
| 2003/0096429 A1 | 5/2003 | Baeumner et al. | |
| 2004/0161788 A1* | 8/2004 | Chen et al. | 435/6 |
| 2006/0084165 A1 | 4/2006 | Lee et al. | |
| 2006/0094051 A1 | 5/2006 | Lee et al. | |
| 2006/0110725 A1 | 5/2006 | Lee et al. | |
| 2006/0188876 A1 | 8/2006 | Kilaas et al. | |

OTHER PUBLICATIONS

Rudi et al.; "Rapid, Universal Method to Isolate PCR-Ready DNA using Magnetic Beads" Biotechniques; vol. 22; pp. 506-511; Mar. 1997.

Taylor et al.; "Lysing Bacterial Spores by Sonication through a Flexible Interface in a Microfluidic System" Anal. Chem.; vol. 73; pp. 492-496; 2001.

Hofmann, O., et al.; "Laser Based Disruption of Bacillus Spores on a Microchip"; 8th International Conference on Miniaturized Systems for Chemistry and Life Sciences; Sep. 26-30, 2004; Royal Society of Chemistry; pp. 258-260; 2005.

Elgort, M.G., et al.; "Extraction and Amplification of Genomic DNA from Human Blood on Nanoporous Aluminum Oxide Membranes"; Clinical Chemistry; vol. 50, No. 10; pp. 1817-1819; 2004.

Li, H., et al.; "Selective genotyping of individual cells by capillary polymerase chain reaction"; Electrophoresis; vol. 23; pp. 3372-3380; 2002.

Safarik, I., et al.; "Biologically Active Compounds and Xenobiotics: Magnetic Affinity Separations"; Encyclopedia of Separation Science, Academic Press; pp. 2163-2170; 2000.

Tian, H., et al.; "Evaluation of Silica Resins for Direct and Efficient Extraction of DNA from Complex Biological Matrices in a Miniaturized Format"; Analytical Biochemistry; vol. 283; pp. 175-191; 2000.

Levison, P.R., et al.; "Recent Developments of Magnetic Beads for Use in Nucleic Acid Purification"; Journal of Chromatography A, vol. 816; pp. 107-111; 1998.

More, M.I., et al.; "Quantitative Cell Lysis of Indigenous Microorganisms and Rapid Extraction of Microbial DNA From Sediment"; Applied and Environmental Microbiology; 60 (5): pp. 1572-1580; May 1994.

Liu, H., et al.; "Self Contained, Fully Integrated Biochip for Sample Preparation, Polymerase Chain Reaction Amplification, and DNA Microarray Detection"; Analytical Chemistry' vol. 76, No. 7; pp. 1824-1831; Apr. 1, 2004.

Huaina Li, et al.; "Spatial Control of Cellular Measurements with the Laser Micropipet"; Anal. Chem.; vol. 73; pp. 4625-4631; 2001.

* cited by examiner

DEVICE AND METHOD FOR RAPIDLY LYSING CELLS OR VIRUSES

CROSS-REFERENCE TO RELATED PATENT APPLICATION

This application claims priority to Korean Patent Application No. 10-2005-0112967, filed on Nov. 24, 2005, in the Korean Intellectual Property Office, and all the benefits accruing therefrom under 35 U.S.C. §119, the disclosure of which is incorporated herein in its entirety by reference.

BACKGROUND OF THE INVENTION

1. Field of the Invention

The present invention relates to a device and a method for rapidly lysing cells or viruses, and in particular, to a cell lysis device for lysing cells or viruses, which comprises a cell lysis tube having a sample inlet; a pump connected to the cell lysis tube for transferring a sample inside the tube; a sealing unit for temporarily sealing a specific region of the cell lysis tube; and a laser source for generating a laser, and a method of rapidly lysing cells or viruses using the cell lysis device.

2. Description of the Related Art

Efficient extraction of DNA from cells is needed in a variety of applications, and inter alia, such extraction of DNA is essential in molecular diagnosis, particularly identification and quantification of pathogenic bacteria. Molecular diagnosis is generally performed by DNA extraction followed by DNA amplification. Exemplary methods for DNA amplification include polymerase chain reaction (PCR), ligase chain reaction, stranded-displacement amplification, nucleic acid-based amplification, repair chain reaction, helicase chain reaction, QB replicase amplification, and ligation activated transcription.

Extraction of DNA from cells has been performed using materials, which have a tendency for DNA binding. Examples of the material used for DNA isolation include silica, glass fiber, anion exchange resins and magnetic beads (Rudi, K. et al., *Biotechniques,* 22, 506-511 (1997); and Deggerdal, A. et al., *Biotechniques,* 22, 554-557 (1997)). For the purpose of avoiding manual operation and eliminating operator errors, several automated machines have been developed for high-throughput DNA extraction.

Cell lysis is conventionally performed using mechanical, chemical, thermal, electrical, ultrasonic and microwave methods (Michael T. Taylor et al., *Anal. Chem.,* 73, 492-496 (2001)).

Chemical methods for cell lysis involve the use of a lysing agent for disrupting cells and releasing DNA. Further, additional treatment of cell extract is required using a chaotropic reagent to denature proteins in the cell extract. One disadvantage with the chemical methods for cell lysis is that harsh chemicals are used to disrupt cells. Such chemicals may impede a PCR reaction that is performed using the cell extract after the cell lysis, and thus, purification of the DNA from the cell extract is necessary before performing the PCR reaction. Furthermore, chemical methods for cell lysis are labor-intensive, time-consuming and costly, and often produce low DNA recovery yields.

Thermal methods for cell lysis involve repeated freeze-thaw cycles. One disadvantage with the thermal method is that the method is often unable to disrupt many intracellular structures. Heating is an alternative method of disrupting the cell walls or cell membranes. One disadvantage with such a method is that heating causes denaturation of proteins, which may adhere to the released DNA, and thereby hinder DNA amplification.

The ultrasonic method is an alternative physical method for disrupting cells and releasing DNA. For the ultrasonic method, a cell solution or a cell suspension is placed in the chamber of an ultrasonic water bath. Ultrasonic cell destruction is highly ineffective in cell lysis. First, the energy distribution of an ultrasound is not uniform, and such non-uniform distribution of ultrasonic energy induces results that lack consistency. Further, the ultrasonic water bath is incapable of concentrating the ultrasonic energy into the cell solution container, and it usually takes several minutes to achieve complete disruption of the cells. Finally, ultrasonic cell destruction produces a sound that is unpleasant to human ears.

An alternative method for disrupting cells and releasing DNA employs a laser. An existing method for cell lysis using a laser is problematic in that irradiation of the cell solution with the laser causes an increase in the vapor pressure of the cell solution, and results in loss of the cell solution due to evaporation. The existing method employs a process of sealing the cell solution container with optic tape to prevent the loss of the cell solution by evaporation, but this taping process requires manual adhesion and removal of the tape.

SUMMARY OF THE INVENTION

In one embodiment, the invention provides a cell lysis device for lysing cells or viruses rapidly and conveniently. The cell lysis device comprises a cell lysis tube with a sample inlet; a pump connected to the cell lysis tube for transferring the sample in the cell lysis tube; a sealing unit for temporarily sealing a specific region of the cell lysis tube; and a laser source for generating a laser.

In an alternative embodiment, the invention also provides a method of lysing cells or viruses rapidly and conveniently using the cell lysis device.

In one embodiment the method of lysing cells or viruses using the cell lysis device comprises introducing a sample containing cells or viruses, and optionally magnetic beads, to a cell lysis tube through a sample inlet; transferring the sample by means of a pump to a region of the cell lysis tube where a laser can irradiate the sample; sealing the region of the cell lysis tube where the sample is placed with the sealing unit; irradiating the sample with the laser; removing the sealing unit from the cell lysis tube; and discharging the sample from the cell lysis tube by means of the pump. In another embodiment, the method of lysing cells or viruses comprises introducing a sample containing cells or viruses and magnetic beads to the cell lysis tube through the sample inlet; transferring the sample by means of the pump to a region of the cell lysis tube where a laser can irradiate the sample; sealing the region of the cell lysis tube where the sample is placed with the sealing unit; irradiating the sample with the laser; removing the sealing unit from the cell lysis tube; attaching a magnet to the region of the cell lysis tube where the sample is placed to remove the magnetic beads from the sample; and discharging the sample from the cell lysis tube by means of the pump.

DETAILED DESCRIPTION OF THE INVENTION

Figure 1A:
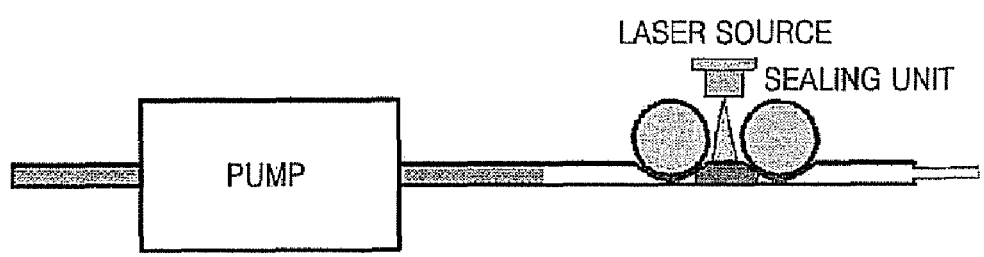
FIG. 1A and FIG. 1B are schematic diagrams showing functional elements of an exemplary embodiment of a cell lysis device for lysing cells or viruses according to the invention.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In one embodiment the invention provides a cell lysis device for lysing cells or viruses comprising a cell lysis tube with a sample inlet; a pump connected to the cell lysis tube for transferring a sample into the cell lysis tube; a sealing unit for reversibly sealing a specific region of the cell lysis tube; and a laser source for generating a laser.

In another embodiment the invention provides a method of lysing cells or viruses using the cell lysis device comprising introducing a sample containing cells or viruses, and optionally magnetic beads, to a cell lysis tube through a sample inlet; transferring the sample by means of a pump to a region of the cell lysis tube where a laser can irradiate the sample; sealing the region of the cell lysis tube where the sample is placed with the sealing unit; irradiating the sample with the laser; removing the sealing unit from the cell lysis tube; and discharging the sample from the cell lysis tube by means of the pump.

In another embodiment the invention provides a method of lysing cells or viruses using the cell lysis device comprising introducing a sample containing cells or viruses, and magnetic beads, to a cell lysis tube through a sample inlet; transferring the sample by means of a pump to a region of the cell lysis tube where a laser can irradiate the sample; sealing the region of the cell lysis tube where the sample is placed with the sealing unit; irradiating the sample with the laser; removing the sealing unit from the cell lysis tube; attaching a magnet to the region of the cell lysis tube where the sample is placed to remove the magnetic beads from the sample; and discharging the sample from the cell lysis tube by means of the pump.

When the device or method for lysing cells or viruses is used according to the invention, the lysis of cells or viruses can be performed more conveniently and more rapidly.

According to one embodiment of the invention, a cell lysis device for lysing cells or viruses comprises a cell lysis tube, a pump for transferring the sample, a sealing unit for immobilizing the sample, and a laser source for lysing cells.

In one embodiment, the cell lysis tube of the cell lysis device has a sample inlet at one end of the cell lysis tube, and the sample inlet serves not only as the inlet for the sample, but also as an outlet for discharging the sample from the cell lysis tube after completion of the cell lysis. Further, while one end of the cell lysis tube includes the sample inlet, the other end of the cell lysis tube is connected to the pump for transferring the sample. The cell lysis tube can be made of a hydrophobic material, because a tube made of a hydrophobic material can prevent diffusion of the sample therein. In an exemplary embodiment, the cell lysis tube can be formed of a light-transmissive material so that the cell lysis tube is suitable for laser irradiation. The cell lysis tube can also be sufficiently flexible such that the sealing unit can reversibly seal the cell lysis tube. Examples of material that the cell lysis tube can be made from include Tygon® tubing, silicone tubing, and the like.

In one embodiment, the cell lysis tube in the cell lysis device may have a sample inlet. The sample inlet has a smaller outer diameter than the other part of the cell lysis tube. The sample inlet can be a tip made of a hard material.

When a tip made of a hard material and having a smaller outer diameter is used for the sample inlet of the cell lysis tube, the operation of introducing the sample into the cell lysis tube, or the operation of discharging the sample from the tube, becomes more convenient. In addition, since the method of cell lysis using a laser handles a small sample volume, such as a few microliters, the inner diameter of the cell lysis tube should be small. However, since tubing comprising an outer diameter of 2 mm or more is generally used for the cell lysis tube to provide mechanical strength, it can be difficult to insert the cell lysis tube into a sample container in order to draw the sample into the cell lysis tube. Therefore, utilizing a tip with an outer diameter smaller than that of the cell lysis tube is recommended.

The cell lysis device of the invention includes a pump connected to the cell lysis tube, which is capable of transferring the sample into the cell lysis tube. Exemplary pumps which may be used, include, for example a peristaltic pump, a membrane pump, or a syringe pump, preferably a peristaltic pump.

The sealing unit of the cell lysis device according the invention is capable of reversibly isolating a specific region in the cell lysis tube from the other regions in the cell lysis tube. The sealing unit can be coupled to a laser source, which is used for irradiating the sample. As noted above, evaporation of the sample, which is in a solution form, may occur due to an increase in the vapor pressure of the sample solution during the laser irradiation. The sealing unit can be used to prevent evaporation of the sample. Conventional cell lysis devices that use a laser to disrupt cells make use of optic tape to solve the problem of increased vapor pressure due to the laser irradiation, and the process of adhering and removing the optic tape is performed entirely by manual operation, which is rather complicated and inconvenient. In contrast, the sealing unit applicable to the cell lysis device according to the invention can be operated as an automated system and does not have the problems of conventional cell lysis devices.

Figure 1B:
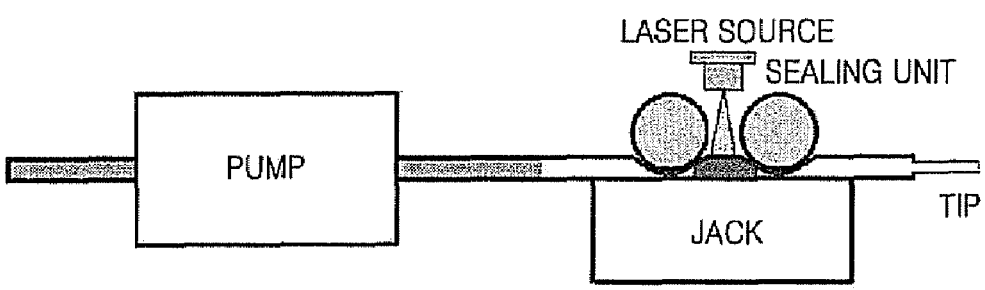
Figure 2:
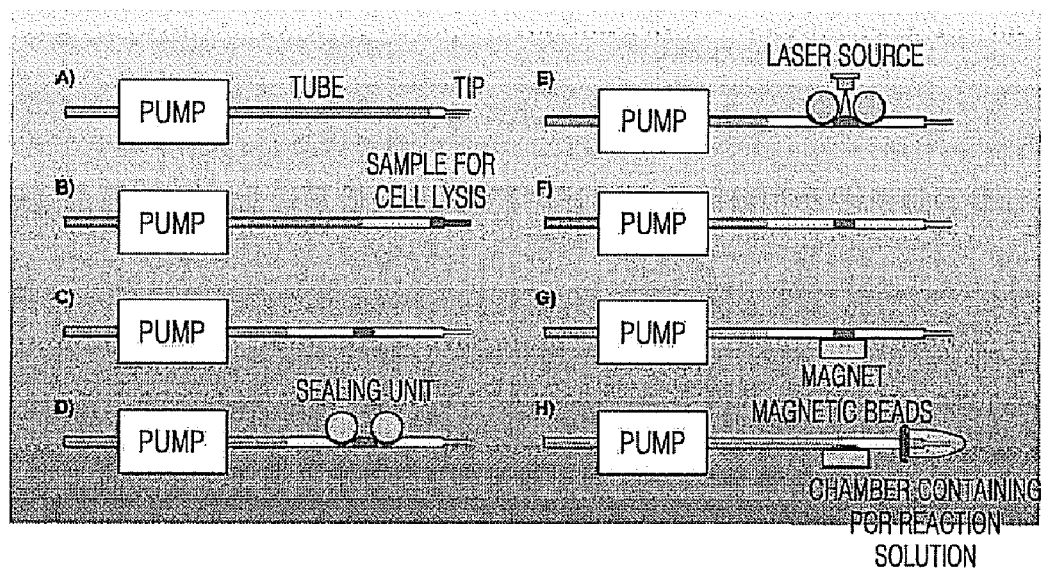
FIG. 2 is a diagram showing an exemplary embodiment of a method of lysing cells or viruses according to the invention.
Figure 3:
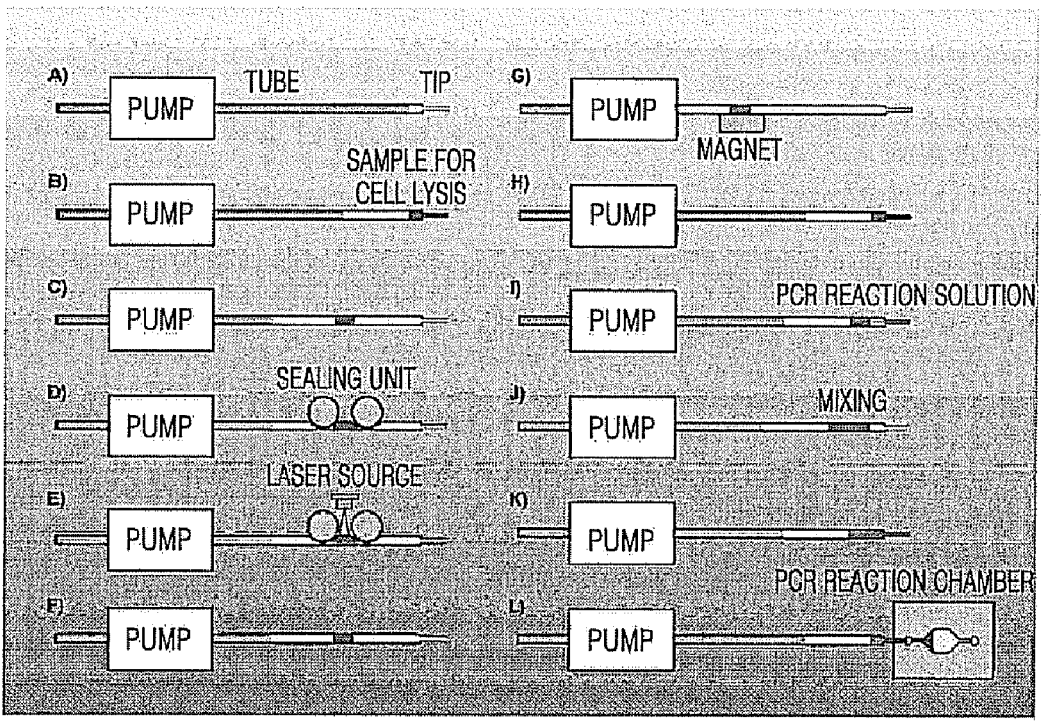
FIG. 3 is a diagram showing another exemplary embodiment of a method of lysing cells or viruses according to the invention.
Figure 4:
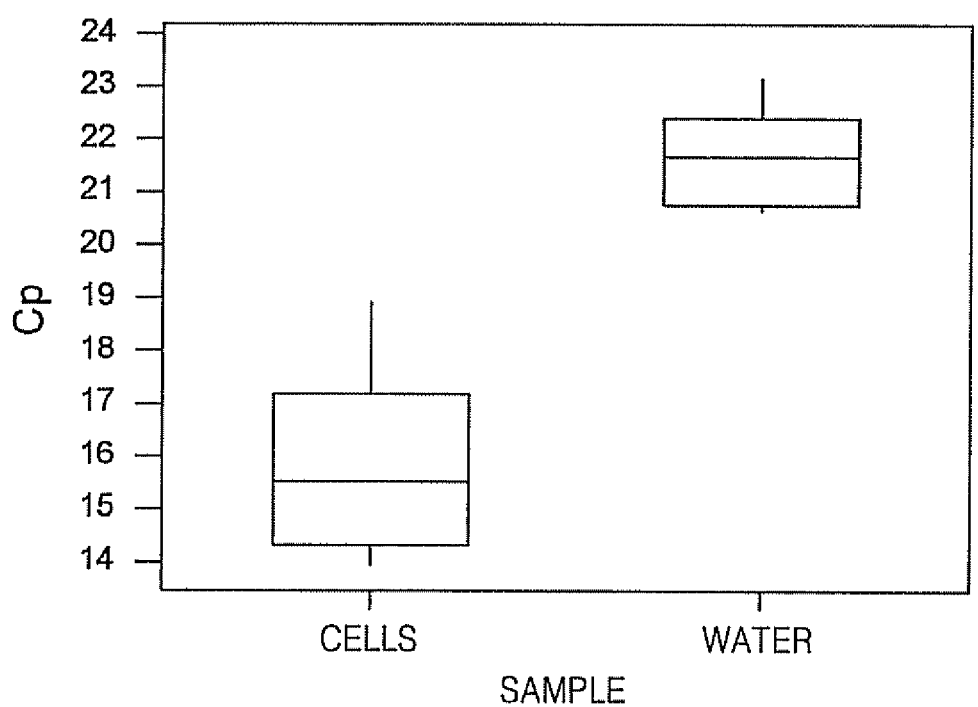
FIG. 4 is a graph showing the cross point (Cp) of PCR reactions performed using water and lysed cells using a method of lysing cells or viruses according to the invention.

The sealing unit may be used to reversibly seal the cell lysis tube, (i) by moving the sealing unit toward the cell lysis tube which is immobilized; or (ii) by moving the cell lysis tube toward the sealing unit which is immobilized, in order for the sealing unit to press against the cell lysis tube and temporarily seal a specific region of the cell lysis tube (See FIG. 1B).

In one embodiment, the sealing unit includes two rods that are designed to press down a specific region of the cell lysis tube (the region of laser irradiation) from above. Thus, when the sample is introduced to the specific region, the rods press down on the cell lysis tube at the ends of the specific region to immobilize the sample within the specific region of the cell lysis tube, and then, the process of cell lysis by laser irradiation can be performed.

The cell lysis device of the invention also includes a laser source connected to the cell lysis tube for irradiating a laser. An exemplary laser source includes, for example, a laser diode which may permit miniaturizing the cell lysis device.

In addition, one embodiment of the cell lysis device may further comprise a magnet for removing magnetic beads from the sample. After the process of laser irradiation of the sample to achieve cell lysis, a magnet may be attached to an external side of the cell lysis tube, so that the magnetic beads contained in the sample are attracted to the site of the attached magnet, and thus the magnetic beads can be removed.

In another embodiment, a vibrator may be also added on the outside of the cell lysis tube, in order to mix the sample. It is envisioned that the vibrator can also be used to mix the sample with other solutions within the cell lysis tube after completion of the cell lysis, for example a PCR reaction solution. The vibrator may be, for example a vibrator utilizing a magnetic field, a vibrator utilizing an electric field, or a mechanical vibrator.

In an exemplary embodiment, the cell lysis device of the invention is an automated system for lysing cells or viruses rapidly and conveniently, and is effective for automation of an overall sample pretreatment system.

According to an embodiment of the invention, a method of lysing cells or viruses using the cell lysis device is also provided. According to the current embodiment of the present invention, a sample containing cells or viruses, and optionally magnetic beads is first fed to the cell lysis tube through the sample inlet.

The magnetic beads, which are optionally contained in the sample, can comprise a size of about 50 nm to about 1,000 µm, preferably, about 500 nm to about 50 µm. Furthermore, the magnetic beads can be formed from at least one substance selected from the group consisting of Fe, Ni, Cr and oxides thereof, all of which are ferromagnetic. Alternatively, the magnetic beads can be formed from a material selected from polymers, organic materials, silicon and glass, which are then coated with a ferromagnetic metal.

When a laser irradiates the magnetic beads contained in the sample, the magnetic beads are heated. The heated magnetic increase the temperature of the sample, and the hot magnetic beads themselves disrupt the cells or viruses in the sample. The magnetic beads in the sample are intended, not only for use as a mere heat energy carrier, but to transfer thermal, mechanical and physical effects to the cell surfaces and to thereby disrupt the cell surfaces more effectively.

Furthermore, when magnetic beads are used, subsequent steps of DNA isolation can be reduced because the process of cell lysis using a laser and magnetic beads results in protein denaturation. The denatured proteins and cell debris attach to the magnetic beads, which can be removed by gravity or magnetic force. This process of using magnetic beads as part of the disclosed method of lysing cells or viruses lowers the limits of detection even further, significantly reduces the time for DNA extraction by eliminating a step from the DNA extraction process, and remarkably facilitates the PCR analysis by increasing the signal amplitude of the extracted DNA.

The cell lysis tube to which the sample is introduced can contain a washing solution. An exemplary washing solution includes, for example, water or alcohol. As the washing solution is moved by the pump, the sample can move along in the cell lysis tube. Furthermore, the washing solution can also be used to wash away any impurities generated by the cell lysis reaction, which remain in the cell lysis tube. In one embodiment, after the cell lysis tube is filled with the washing solution, the sample inlet part is filled with air, or other inert gas, in order to inhibit the contact of the sample with the washing solution, and subsequently the sample is fed to the cell lysis tube.

The cell lysis tube can be made of a hydrophobic material, because a tube made of a hydrophobic material can prevent diffusion of the sample therein. In addition, the cell lysis tube can be formed of a light-transmissive material so that the cell lysis tube is suitable for laser irradiation. The cell lysis tube can also be sufficiently flexible so that the cell lysis tube can be temporarily sealed by the sealing unit. Examples of materials to form the cell lysis tube of the present invention include Tygon® tube, silicone tube, and the like.

When the sample is introduced to the cell lysis tube, the pump operates to transfer the sample to a specific region within the cell lysis tube. The sample is transferred to a position where a laser can irradiate and lyse the cells or viruses. Any conventionally used pump can be used for the invention. The pump may be, for example, a peristaltic pump, a membrane pump or a syringe pump. In an exemplary embodiment, the pump is a peristaltic pump.

When the sample is transferred to the specific position within the cell lysis tube, the region where the sample is placed is temporarily sealed by the sealing unit. When a flexible tube is used, it is possible to reversibly seal the region where the sample is placed, by means of the sealing unit. An exemplary sealing unit may include two rods, as illustrated in FIG. 1A and FIG. 1B. According to one embodiment, the sealing unit serves as a means for preventing the generation of air bubbles, which are generated when the sample is heated by the laser, and which can allow the sample to escape from the position of laser irradiation and from receiving sufficient energy. The sealing unit is required to be able to withstand a pressure greater than or equal to steam pressure.

The sealing unit may be used to temporarily seal the cell lysis tube, (i) by moving the sealing unit against the cell lysis tube which is immobilized; or (ii) by moving the cell lysis tube toward the sealing unit which is immobilized, in order for the sealing unit to press against the cell lysis tube and temporarily seal a specific region of the cell lysis tube (See FIG. 1B).

After the region where the sample is placed is temporarily sealed using the sealing unit, the sample is irradiated with a laser. Since the laser is used to irradiate the cell or virus sample from the outside of the cell lysis tube, it is more effective to use a light-transmissive tube as the cell lysis tube.

Cell lysis is performed by irradiating the cell sample with a laser beam, and thus, such laser irradiation causes an increase in the temperature of the sample, and a subsequent increase in the vapor pressure. Using the sealing unit as described above can solve the problem of vapor pressure increase.

After the irradiation of the sample with the laser, the sealing unit is removed from the cell lysis tube. In some embodiments, a magnet is attached to the external side of the cell lysis tube to remove magnetic beads from the sample.

Then the pump is operated to discharge the sample from the cell lysis tube. Then, the sample may be transferred to a PCR reaction chamber.

In another embodiment, a process of introducing a PCR reaction solution directly into the cell lysis tube and mixing the PCR reaction solution with the sample containing lysed cells, may optionally be further performed before the process of discharging the sample from the cell lysis tube. Further, without being limited thereto, the sample and the PCR reaction solution can be mixed using a vibrator or the like. Exemplary vibrators, which can be used for this purpose, include, for example, a vibrator utilizing a magnetic field, a vibrator utilizing an electric field, a mechanical vibrator, or the like. Furthermore, after the mixing of the sample containing lysed cells with the PCR reaction solution, the mixture can be transferred to a PCR reaction chamber.

The present invention will now be described in more detail with reference to the following Examples. These Examples are for illustrative purposes only and are not intended to limit the scope of the present invention.

EXAMPLE 1

Cell Lysis Device

The elements of a cell lysis device according to Example 1 comprise the following:

Cell Lysis Tube: Tygon® R-3607, inner diameter 0.38 mm, outer diameter 2.20 mm, length 400 mm;

Sample Inlet (Tip structure): Poly(ether ether ketone) (PEEK) tube, inner diameter 0.4 mm, outer diameter 0.25 inch;

Pump: Peristaltic pump (ISM596A, Ismatec S A, Switzerland);

Sealing unit: two rods (SUS rod), diameter 0.5 inch, interval between the centers of the rods: 25 mm;

Laser source: Laser diode L8446-42 (Hamamatsu Photonics K. K.).

Additionally, the cell lysis device used in the examples below comprised a magnet.

EXAMPLE 2

Cell Culture

Cells of *Streptococcus mutans*, for subjection to cell lysis using the device and method of the invention, were cultured in a brain heart infusion (BHI) medium at 37° C. under vigorous aerobic conditions, until the logarithmic phase was reached ($OD_{600}$=0.5 to 1.0). The cells were harvested by centrifugation and were washed two times with 3 ml of phosphate buffered saline (PBS). The washed cells were resuspended in PBS.

EXAMPLE 3

Confirmation of Cell Lysis

The cell lysis tube was filled with water by operating the peristaltic pump of the cell lysis device produced in Example 1. Next, air was introduced into the cell lysis tube in order to prevent contact between the water and the sample.

Subsequently, a sample solution was prepared by mixing the cells cultured in Example 2 and magnetic beads (size: 1 μm, MyOne™ carboxylic acid, Invitrogen Corporation, Norway) to a final concentration of $1 \times 10^8$ cells/ml and 10 beads/μl, respectively. A volume of 3.9 μl of the sample was introduced into the cell lysis tube through the tip of the sample inlet.

The sample was transferred to a specific position (position of laser irradiation) in the cell lysis tube, by operating the peristaltic pump in the cell lysis device.

Then the two rods of the sealing unit were used to temporarily seal the region of the tube where the sample was placed.

Then a laser diode was used to irradiate the sample at a power output of 0.8 W for 40 seconds.

After irradiating the sample using the laser diode, the sealing unit temporarily sealing the cell lysis tube was removed, and a magnet was attached to the position of the sample to remove the magnetic beads contained in the sample. Subsequently, the pump was operated to transfer the from the cell lysis tube to a PCR reaction chamber for use in a PCR reaction and to transfer the washing solution in the cell lysis tube to wash the cell lysis tube at the region of the laser irradiation.

In order to measure the degree of cell lysis more accurately, the crossing point (Cp) value for a DNA amplification was measured (See Table 1). DNA amplification was performed using the real-time PCR apparatus, LIGHTCYCLER® (Roche Corporation, Ind., US). The Cp value is such that, when the initial DNA concentration is higher, the fluorescent signal is detected at a smaller Cp value; and when the initial DNA concentration is lower, the fluorescent signal is detected at a larger Cp value. The Cp value is also relevant to the purity of the DNA. For example, when materials hindering PCR are removed from a sample resulting in DNA of high purity, the Cp value decreases. Similarly, when materials hindering PCR are not removed from the sample and the level of DNA purity remains low, the Cp value increases.

After disrupting the bacterial cells using the method as described above, PCR was performed, and the Cp values were measured. Results presenting the determined Cp are provided in Table 1 below. Water was used as a negative control. The Cp values were measured for the negative control in the same manner as described above. As an additional control, the same procedure was performed with cells and water, except that for this control the process of laser irradiation was omitted for the cells as well as for the water. The Cp values were measured for the controls, the results of which are presented in Table 1.

TABLE 1

| Sample | Cells + Magnetic beads | Negative Control |
|---|---|---|
| Laser irradiation | 15.83 | 23.18 |
| | 14.63 | 21.86 |
| | 13.91 | 21.53 |
| | 15.56 | 20.68 |
| | 14.80 | 21.67 |
| | 13.97 | 22.65 |
| | 18.52 | 20.62 |
| | 18.91 | 22.16 |
| | 15.52 | 20.85 |
| No laser irradiation | 19.23 | 20.97 |

As shown in Table 1, the Cp values for the PCR performed with the cells irradiated with the laser were lower than the Cp value for the cells which were not irradiated with the laser. Thus, it is evident that efficient cell lysis was achieved by the laser irradiation. On the other hand, when water was used as the negative control, the Cp values were approximately constant, regardless of the presence or absence of laser irradiation.

Thus, it can be seen that cells can be lysed efficiently using the cell lysis device and method of the invention.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cell lysis device for lysing cells or viruses, comprising:
   a cell lysis tube having a sample inlet at one end of the cell lysis tube;
   a pump connected to a second end of the cell lysis tube for transferring a sample into the tube;
   a sealing unit for reversibly sealing a specific region of the tube, wherein the sealing unit comprises two rods positioned perpendicularly to the longitudinal axis of the cell lysis tube such that the centers of the rods are separated by a distance along the longitudinal axis of the cell lysis tube, such that when the two rods press against the cell lysis tube each end of the specific region is sealed by one of the two rods and removal of the rods from the cell lysis tube reverses the seal; and
   a laser source connected to the cell lysis tube for irradiating a sample in the specific region.

2. The device of claim 1, further comprising a magnet on an external surface of the cell lysis tube.

3. The device of claim 1, wherein the cell lysis tube is made of a transparent and flexible material.

4. The method of claim 1, wherein the cell lysis tube is made of a hydrophobic material.

5. The device of claim 1, wherein the sample inlet of the cell lysis tube consists of a tip having a smaller outer diameter than the cell lysis tube.

6. The device of claim 5, wherein the tip is made of a hard material.

7. The device of claim 1, wherein the pump comprises a peristaltic pump, a membrane pump, or a syringe pump.

8. The device of claim 7, wherein the pump is a peristaltic pump.

9. The device of claim 1, further comprising a vibrator for mixing the sample and a PCR reaction solution.

10. The device of claim 9, wherein the vibrator is selected from the group consisting of a vibrator utilizing a magnetic field, a vibrator utilizing an electric field, and a mechanical vibrator.

11. A method of lysing cells or viruses, the method comprising:
    introducing a sample containing cells or viruses and magnetic beads to the cell lysis tube of the cell lysis device of claim 1 through the sample inlet;
    transferring the sample to a specific region on the lysis tube by means of the pump;
    sealing a region of the cell lysis tube where the sample is placed with the sealing unit;
    irradiating the sample with the laser source;
    removing the sealing unit from the cell lysis tube;
    attaching a magnet to the region of the cell lysis tube where the sample is placed to remove magnetic beads from the sample; and
    discharging the sample from the cell lysis by means of the pump.

12. A method of claim 11, further comprising introducing a washing solution into the lysis tube.

13. The method of claim 12, wherein the washing solution is water or alcohol.

14. The method of claim 11, wherein the size of the magnetic beads is about 50 nm to about 1,000 µm.

15. The method of claim 14, wherein the size of the magnetic beads is about 500 nm to about 50 µm.

16. The method of claim 11, wherein the magnetic beads are formed from at least one material selected from the group consisting of Fe, Ni, Cr and oxides thereof.

17. The method of claim 11, wherein the magnetic beads are formed from a material selected from the group consisting of polymers, organic materials, silicon and glass, and then are coated with a ferromagnetic metal.

18. The method of claim 11, wherein the magnetic beads have hydrophilic and negatively charged functional groups on the surface thereof.

19. The method of claim 11, further comprising
    mixing the sample with a solution, before discharging the sample from the cell lysis tube.

20. The method of claim 19, wherein the solution is a PCR reaction solution.

21. A method of lysing cells or viruses, the method comprising:
    introducing a sample containing cells or viruses to the cell lysis tube of the cell lysis device of claim 1 through the sample inlet;
    transferring the sample to a specific region of the cell lysis tube by means of the pump;
    sealing a region of the cell lysis tube where the sample is placed with the sealing unit;
    irradiating the sample with the laser source;
    removing the sealing unit from the cell lysis tube; and
    discharging the sample from the cell lysis tube by means of the pump.

* * * * *